US008906699B2

(12) United States Patent
Naasani

(10) Patent No.: US 8,906,699 B2
(45) Date of Patent: *Dec. 9, 2014

(54) FUNCTIONALIZED FLUORESCENT NANOCRYSTAL COMPOSITIONS AND METHODS FOR THEIR PREPARATION

(75) Inventor: Imad Naasani, Manchester (GB)

(73) Assignee: Life Technologies Corporation, Carlsbad, CA (US)

( * ) Notice: Subject to any disclaimer, the term of this patent is extended or adjusted under 35 U.S.C. 154(b) by 192 days.

This patent is subject to a terminal disclaimer.

(21) Appl. No.: 13/597,056

(22) Filed: Aug. 28, 2012

(65) Prior Publication Data

US 2013/0034916 A1    Feb. 7, 2013

Related U.S. Application Data

(63) Continuation of application No. 11/685,343, filed on Mar. 13, 2007, now Pat. No. 8,283,179, which is a continuation of application No. 10/409,940, filed on Apr. 9, 2003, now Pat. No. 7,205,048, which is a continuation of application No. 10/245,082, filed on Sep. 17, 2002, now Pat. No. 6,955,855, said application No. 11/685,343 is a continuation of application No. 10/410,108, filed on Apr. 9, 2003, now Pat. No. 7,214,428, which is a continuation-in-part of application No. 10/245,082, filed on Sep. 17, 2002, now Pat. No. 6,955,855, said application No. 11/685,343 is a continuation of application No. 10/952,701, filed on Sep. 29, 2004, now Pat. No. 7,198,847, which is a continuation of application No. 10/245,082, filed on Sep. 17, 2002, now Pat. No. 6,955,855.

(60) Provisional application No. 60/379,208, filed on May 9, 2002, provisional application No. 60/322,982, filed on Sep. 17, 2001.

(51) Int. Cl.
*G01N 21/64* (2006.01)
*G01N 33/58* (2006.01)
*B82Y 15/00* (2011.01)

(52) U.S. Cl.
CPC ............. *G01N 33/588* (2013.01); *B82Y 15/00* (2013.01)
USPC ............ 436/501; 428/402; 428/403; 428/407

(58) Field of Classification Search
USPC .................................. 428/402–407; 436/172
See application file for complete search history.

(56) References Cited

U.S. PATENT DOCUMENTS

| 4,469,787 A | 9/1984 | Woods et al. |
| 4,642,334 A | 2/1987 | Moore et al. |

(Continued)

FOREIGN PATENT DOCUMENTS

| WO | WO-00/17655 | 3/2000 |
| WO | WO-00/27365 | 5/2000 |
| WO | WO 00/27365 | * 5/2000 |

OTHER PUBLICATIONS

English Abstract of JP 04059886, Feb. 1992, Funayama et al.*

(Continued)

*Primary Examiner* — Ronak Patel
(74) *Attorney, Agent, or Firm* — Life Technologies Corporation

(57) ABSTRACT

The present invention provides for functionalized fluorescent nanocrystal compositions and methods for making these compositions. The compositions are fluorescent nanocrystals coated with at least one material. The coating material has chemical compounds or ligands with functional groups or moieties with conjugated electrons and moieties for imparting solubility to coated fluorescent nanocrystals in aqueous solutions. The coating material provides for functionalized fluorescent nanocrystal compositions which are water soluble, chemically stable, and emit light with a high quantum yield and/or luminescence efficiency when excited with light. The coating material may also have chemical compounds or ligands with moieties for bonding to target molecules and cells as well as moieties for cross-linking the coating. In the presence of reagents suitable for reacting to form capping layers, the compounds in the coating may form a capping layer on the fluorescent nanocrystal with the coating compounds operably bonded to the capping layer.

19 Claims, 4 Drawing Sheets

(56) References Cited

U.S. PATENT DOCUMENTS

| | | | |
|---|---|---|---|
| 4,946,778 | A | 8/1990 | Ladner et al. |
| 5,034,506 | A | 7/1991 | Summerton et al. |
| 5,151,507 | A | 9/1992 | Hobbs et al. |
| 5,187,085 | A | 2/1993 | Lee |
| 5,505,928 | A | 4/1996 | Alivisatos et al. |
| 5,558,991 | A | 9/1996 | Trainor |
| 5,596,086 | A | 1/1997 | Matteucci et al. |
| 5,602,240 | A | 2/1997 | De Mesmaeker et al. |
| 5,637,258 | A * | 6/1997 | Goldburt et al. ....... 252/301.4 R |
| 5,679,785 | A | 10/1997 | Engels |
| 5,736,137 | A | 4/1998 | Anderson |
| 5,789,157 | A | 8/1998 | Jensen et al. |
| 5,948,386 | A | 9/1999 | Katti |
| 5,969,135 | A | 10/1999 | Ramasamy |
| 5,990,479 | A | 11/1999 | Weiss et al. |
| 6,114,038 | A | 9/2000 | Castro et al. |
| 6,179,912 | B1 | 1/2001 | Barbera-Guillem et al. |
| 6,221,602 | B1 | 4/2001 | Barbera-Guillem et al. |
| 6,261,779 | B1 * | 7/2001 | Barbera-Guillem et al. 435/6.11 |
| 6,306,610 | B1 | 10/2001 | Bawendi et al. |
| 6,319,426 | B1 * | 11/2001 | Bawendi et al. ....... 252/301.4 R |
| 6,326,144 | B1 | 12/2001 | Bawendi et al. |
| 6,855,551 | B2 | 2/2005 | Bawendi et al. |
| 6,972,326 | B2 | 12/2005 | Haugland et al. |
| 2003/0059635 | A1 | 3/2003 | Naasani |
| 2004/0178390 | A1 * | 9/2004 | Whiteford et al. ............ 252/500 |

OTHER PUBLICATIONS

EP09172526.7, "Extended European Search Report, mailed Jan. 29, 2010", 7 Pages.

Adair, John R. , "Engineering Antibodies for Therapy", *Immunological Reviews*, vol. 130, 1992, 5-40.

Aldana, Jose et al., "Photochemical Instability of CdSe Nanocrystals Coated by Hydrophilic Thiols", *J. Am. Chern. Soc.*, vol. 123, No. 36, 2001, 8844-8850.

Bruchez, M et al., "Semiconductor Nanocrystals as Fluorescent Biological Labels", *Science*, vol. 281., Sep. 25, 1998, 2013-2016.

Business Communications Co. "Coatings and Polymers: Nanocrystal Particles Serve as Phosphors", *Optical Materials and Engineering News*, vol. 5, No. 12, Aug. 1995, 1-2.

Chan, et al., "Quantum Dot Bioconjugates for Ultrasensitive Nonisotopic Detection", *Science*, vol. 281, No. 5385, Sep. 25, 1998, pp. 2016-2018.

Chan, Warren C. et al., "One-step conjugation of biomolecules to luminescent nanocrystals. In Molecular Imaging: Reporters, Dyes, Markers, and Instrumentation", *Proceedings of SPIE*, vol. 3924, 2000, 2-9.

Dabbousi, B. O. et al., "(Cdse)Zns Core-Shell Quantum Dots: Synthesis and Characterizations of a Size Series of Highly Luminescent Nanocrystallites", *J. Phys. Chem. B*, vol. 101, No. 46, Jun. 26, 1997, 9463-9475.

Danek, Michal et al., "Synthesis of Luminescent Thin-Film CdSe/ZnSe Quantum dot composites Using CdSe Quantum Dots Passivated with an Overlayer of ZnSe", *Chemistry of Materials*, vol. 8, No. 1, 1996, 173-180.

Efros, A. et al., "Band-edge exciton in quantum dots of semiconductors with a degenerate valence band: dark and bright exciton states", *Physical Review B*. vol. 54, Issue 7, 1996, 4843-4856.

Empedocles, Stephen A. et al., "Photoluminescence Spectroscopy of Single CdSe Nanocrystallite Quantum Dots", *Physical Review Letters*, vol. 77, No. 18, Oct. 28, 1996, 3873-3876.

EP02803277, , "European Search Report mailed on Jan. 26, 2005", 3.

Gali, Hariprasad et al., "Synthesis, Characterization, Labeling with 99mTc/188Re of Peptide Conjugates Containing a Dithia-bisphosphine Chelating Agent", *Bioconjugate Chem.*, vol. 12, No. 3, 2001, 354-363.

Giuliano, K. A. et al., "Fluorescent-Protein Biosensors: New Tools for Drug Discovery", *Trends in Biotechnology*, vol. 16, No. 3, XP004108592, Elsevier Publications, 16(3), 1998, 135-140.

Hines, Margaret A. et al., "Synthesis and Characterization of Strongly Luminescing ZnS-Capped CdSe Nanocrystals", *J. Phys. Chem.*, vol. 100, No. 2, 1996, 468-471.

Kho, R. et al., "Zinc-histidine as nucleation centers for growth of ZnS nanocrystals", *Biochemical and Biophysical Research Communications*, vol. 272, No. 1, 2000, 29-35.

Kho, Richard et al., "ZIno-Histidine as Nucleation Centers for Growth of ZnS: Nanocrystals", *Biochemical and Biophysical Research Communications*, vol. 272(1), 2000, 29-35.

Murakoshi, et al., "Control of Surface Coverage and Solubility of Thiophenolate-Capped CdS Nanocrystallites", *J. Colloid Interface Sci.* 203, 1998, 225-228.

Murray, et al., "Synthesis and Characterization of Nearly Monodisperse CdE (E=S, Se, Te) Semiconductor Nanocrystallites", *J. Am. Chem. Soc.*,115, 1993, 8706-15.

Murray, C. B. et al., "Self-Organization of CdSe Nanocrystallites into Three-Dimensional Quantum Dot Superlattices", *Science*, Nov. 24, 1995, 1335-1338.

Nirmal, M et al., "Fluorescence intermittency in single cadmium selenide nanocrystals", *Nature*, vol. 383, Oct. 31, 1996, 802-804.

Norris, D J. et al., "Measurement and Assignment of the Size-Dependent Optical Spectrum in CdSe Quantum Dots", *Physical Review B.*, vol. 53, No. 24, 1996, 16338-16346.

Peng, Xiaogang et al., "Epitaxial Growth of Highly Luminescent Nanocrystals with Photostability and Electronic Accessibility", *J. Am. Chem. Soc.*, vol. 119, No. 30, 1997, 7019-7029.

Pluckthun, Andreas , "Mono- and Bivalent Antibody Fragments Produced in *Escherichia coli*: Engineering, Folding and Antigen Binding", *Immunological Reviews*, vol. 130, No. 1, 1992, 151-188.

Rodriguez-Viejo, J. et al., "Cathodoluminescence and photoluminescence of highly luminescent CdSe/ZnS quantum dot composites", *Appl. Phys. Lett.*, vol. 70, No. 16, 1997, 2132-2134.

Sacra, A. et al., "Stark spectroscopy of CdSe nanocrystallites: The significance of transition linewidths", 1995,*I. Chern. Phys. 103*, 1995, 5236-5245.

Singer, et al., "Optimal humanization of 1B4, an anti-CD18 murine monoclonal antibody, is achieved by correct choice of human V-region framework sequences", *J. Immunol.*, vol. 150, No. 7, 1993, 2844-2857.

Stankova, Ivanka G. et al., "Synthesis of thiazole, imidazole and oxazole containing amino acids for peptide backbone modification", *J. Peptide Sci.*, vol. 5, No. 9, 1999, 392-398.

Tsiavaliaris, Georgios et al., "New Bifunctional Chelating Phosphine Ligands for Immobilization of Metal Complexes on Oxidic Supports", *Synlett*, No. 3, 2001, 391-393.

Warren, C. W. et al., "One Step Conjugation of Biomolecules to Luminescent Nanocrystals", vol. 3924, *Proceedings of SPIE, Molecular Imaging.*, 2000, 2-9.

* cited by examiner

FUNCTIONALIZED FLUORESCENT NANOCRYSTAL COMPOSITIONS AND METHODS FOR THEIR PREPARATION

CROSS REFERENCES AND RELATED APPLICATIONS

This application is a continuation of: U.S. Utility patent application Ser. No. 11/685,343, filed Mar. 13, 2007, now U.S. Pat. No. 8,283,179, which is a continuation of U.S. Utility patent application Ser. No. 10/952,701, filed Sep. 29, 2004, now U.S. Pat. No. 7,198,847, which is a continuation of U.S. Utility patent application Ser. No. 10/409,940, filed Apr. 9, 2003, now U.S. Pat. No. 7,205,048, which is a continuation in part of U.S. Utility patent application Ser. No. 10/245,082, filed Sep. 17, 2002, now U.S. Pat. No. 6,955,855 which claims priority from U.S. Provisional Application Ser. No. 60/379,208, filed May 9, 2002, and U.S. Provisional Application Ser. No. 60/322,982, filed Sep. 17, 2001, and U.S. Utility patent application Ser. No. 10/410,108, filed Apr. 9, 2003 which is a continuation in part of U.S. Utility patent application Ser. No. 10/245,082, and U.S. Utility patent application Ser. No. 10/952,701 filed Sep. 29, 2004 which is continuation of U.S. Utility patent application Ser. No. 10/245,082 to all of which priority is claimed and the disclosures of which are incorporated herein by reference in their entirety. Any disclaimer that may have occurred during the prosecution of the above-referenced application(s) is hereby expressly rescinded.

GOVERNMENT INTEREST

This invention was made, in part, with government support under contract DAAD17-01-C-0024 with the United States Army Research Laboratory. The government has certain rights in this invention.

FIELD OF INVENTION

This invention relates to surface modification of nanocrystals with a special chemistry that imparts to the semiconductor nanocrystals properties, which include water solubility, protection from dissolution, protection from photo-auto-oxidation, functionalization, and a marked enhancement of fluorescence intensity.

BACKGROUND OF THE INVENTION

Fluorescence-based analysis has become a powerful tool in scientific research, clinical diagnostics and many industrial applications. However, while fluorescent organic molecules such as fluorescein and phycoerethrin are used frequently in fluorescence detection systems, there are disadvantages in using these molecules separately or in combination. For example, photobleaching (fading of intensity under light sources) is a major problem that hinders the accuracy of quantitative measurements made using these molecules. In addition, each type of fluorescent molecules typically requires excitation with photons of a different wavelength as compared to that required for another type of fluorescent molecules due to the relatively narrow absorption spectrum of each. Moreover, even when a single light source is used to provide a single excitation wavelength, often there is overlapping or insufficient spectral spacing between the emissions of different fluorescent molecules to permit individual and quantitative detection.

Semiconductor nanocrystals are now being evaluated as a promising tool of nonisotopic detection to replace conventional fluorescent molecules. Since the spectral emission characteristics of nanocrystals are a function of the size, nanocrystals produced in a narrow size distribution can be excited to emit a discrete fluorescence peak of narrow bandwidth. In other words, the ability to control the spectral characteristics of nanocrystals (narrow bandwidth, discrete emission wavelengths, a single wavelength can excite an array of nanocrystals with different emissions) is the major attracting point in their use. Another advantage of the nanocrystals is their resistance toward photobleaching under intensive light sources.

Examples of semiconductor nanocrystals are known in the art to have a core selected from the group consisting of CdSe, CdS, CdTe (collectively referred to as "CdX") (see, e.g., Norris et al., 1996, Physical Review B. 53: 16338-16346; Nirmal et al., 1996, Nature 383: 802-804; Empedocles et al., 1996, Physical Review Letters 77: 3873-3876; Murray et al., 1996, Science 270: 1355-1338; Effros et al., 1996, Physical Review B. 54: 4843-4856; Sacra et al., 1996, J. Chem. Phys. 103: 5236-5245; Murakoshi et al., 1998, J. Colloid Interface Sci. 203: 225-228; Optical Materials and Engineering News, 1995, Vol. 5, No. 12; and Murray et al., 1993, J. Am. Chem. Soc. 115: 8706-8714; the disclosures of which are hereby incorporated by reference), and ZnS (Kho et al. 2000, Biochem. Biophys. Research Commun. 272: 29-35).

As known in the art, a manual batch method may be used to prepare semiconductor nanocrystals of relative monodispersity (e.g., the diameter of the core varying approximately 10% between quantum dots in the preparation), as has been described previously (Bawendi et al., 1993, J. Am. Chem. Soc. 115: 8706). Advances in nanocrystal core production and improvements in narrowing the particle size distribution, the controllability of particle size, and the reproducibility of production have been achieved by a continuous flow process (U.S. Pat. No. 6,179,912, the disclosure of which is herein incorporated by reference). Core semiconductor nanocrystals, however, exhibit low fluorescence intensity upon excitation, lack of water solubility, lack of surface functional groups for linking with target molecules, and additionally, susceptibility to dissociation and degradation in aqueous environments with high ionic strength. The low fluorescence intensity has been ascribed to a leak of exciton to the outer phase, to the presence of surface energy states that act as traps which degrade the fluorescence properties of the core nanocrystal, or to intermediate states of non radiative relaxations.

Efforts to improve the fluorescence intensity involve passivating (or capping) the outer surface of a core nanocrystal in order to reduce or eliminate the surface energy states. Inorganic materials with higher band gap energy have been used for passivation; i.e., core nanocrystals have been passivated with an inorganic coating ("shell") uniformly deposited on the surface of the core nanocrystals. The shell which is typically used to passivate CdX core nanocrystals is preferably comprised of YZ wherein Y is Cd, Hg, or Zn, and Z is S, or Se, or Te. However, these passivated semiconductor nanocrystals have been reported to have a limited improvement in fluorescence intensity (with reference to quantum yield), and to have solubility in organic solvents only. Organic molecules, such as tri-n-octyl phosphine (TOP) and tri-n-octyl phosphine oxide (TOPO) have been also used to coat nanocrystals (see Murray et al., 1993, J. Am. Chem. Soc. 115: 8706-8714, Hines and Guyot-Sionnest 1996, J. Phys. Chem. 100: pp 468, Dabbousi et al., 1997, J. Phys. Chem. 101: 9463). Coatings with these molecules have been reported to produce limited improvement in fluorescence intensity, and provide the coated nanocrystals with solubility only in organic solvents.

Furthermore, the molecules coating the nanocrystal are easily displaced by different solvents.

To make fluorescent nanocrystals useful in biological applications or detection systems utilizing an aqueous environment, it is desirable that the fluorescent nanocrystals used in the detection system are water-soluble. "Water-soluble" is used herein to mean sufficiently soluble or suspendable in an aqueous solution, such as in water or water-based solutions or buffer solutions, including those used in biological or molecular detection systems as known by those skilled in the art. Particles and surfaces may also be characterized by their ability to be wet by a fluid. The fluid may be water or a solution of water and other liquids like ethanol. One method to impart water-solubility or wettability to semiconductor nanocrystals (e.g., CdX core/YZ shell nanocrystals) is to exchange the overcoating layer of TOP or TOPO with a coating, or "capping compound", which will impart some water-solubility. For example, a mercaptocarboxylic acid may be used as a capping compound to exchange with the organic layer (see, e.g., U.S. Pat. No. 6,114,038, the disclosure of which is herein incorporated by reference; see also, Chan and Nie, 1998, Science 281: 2016-2018). The thiol group of monothiol capping compound bonds with the Cd—S or Zn—S bonds (depending on the composition of the nanocrystal), creating a coating which is to some extent not easily displaced in solution, and imparting some stability to the nanocrystals in suspension.

Another method to make the CdX core/YZ shell nanocrystals water-soluble or wettable is by the formation of a coating of silica around the semiconductor nanocrystals (Bruchez, Jr. et., 1998, Science 281: 2013-2015; U.S. Pat. No. 5,990,479) utilizing a mercapto-based linker to link the glass to the semiconductor nanocrystals. An extensively polymerized polysilane shell has been reported to impart water solubility or wettability to nanocrystalline materials, as well as allowing further chemical modifications of the silica surface.

Depending on the nature of the coating compound, coated semiconductor nanocrystals which have been reported as water-soluble may have limited stability in an aqueous solution, particularly when exposed to air (oxygen) and/or light. For example, oxygen and light can cause mercapto-based monothiols used in capping and passivation of nanocrystals to become catalytically oxidized, thereby forming disulfides which destabilize the attachment of the coating and might even play a role in oxidizing the core semiconductor (see, e.g., Aldana et al., 2001, J. Am. Chem. Soc. 123: 8844-8850). Thus, oxidation may cause the capping layer to migrate away from the surface of the nanocrystals, thereby exposing the surface of the nanocrystals resulting in "destabilized nanocrystals" that eventually form nonsolubule aggregates with low fluorescence intensity. In addition, current means for passivating semiconductor nanocrystals are still rather inefficient in increasing the fluorescence intensity to a level desired for detection systems (e.g., in providing a significant increase in sensitivity in fluorescence-based detection systems as compared to currently available fluorescent dyes).

As is evident from current progress in the process of producing semiconductor nanocrystals, it is important to supply the nanocrystals with a stable, and protective capping layer to achieve the desired combinations of properties. In other words, it is desirable that the capping layer be designed in such a way that it is able to impart to the semiconductor nanocrystals improvement in fluorescence efficiency (quantum yield); water solubility; stability in aqueous solutions; stability in media with high ionic strength; resistance to the exposure to hostile environment with light, oxygen and ions; and the ability to bind ligands, molecules, probes of various types, and solid supports. Additionally, there remains a need for a nonisotopic detection system which results in generation of a signal comprising fluorescence emission of high intensity; can result in signal amplification; is not limited as to the chemical nature of the target molecule to be detected (e.g., versus detection of nucleic acid molecules only); can be used to bind molecular probes of various types (affinity molecules, oligonucleotides, nucleobases, and the like); and can result in simultaneous detection of more than one type of target molecule by utilizing a class of nonisotopic molecules that may be excited with a single excitation light source and with resultant fluorescence emissions with discrete fluorescence peaks that can be spectrally distinguished from each other (e.g., using detection means for fluorescence that is standard in the art).

It is an object of the present invention to provide fluorescent nanocrystals which provides a combination of properties including a significant enhancement of fluorescence intensity, water solubility, physical and chemical stability, and functionalization.

SUMMARY OF THE INVENTION

The present invention provides for functionalized fluorescent nanocrystal compositions and methods for making these compositions. The compositions are fluorescent nanocrystals coated with at least one material. The coating material has chemical compounds or ligands with functional groups or moieties with conjugated electrons and moieties for imparting high luminescence efficiency and solubility to coated fluorescent nanocrystals in aqueous solutions. The coating material provides for functionalized fluorescent nanocrystal compositions which are water soluble, chemically stable, and emit light with a quantum yield of greater than 10% and preferably greater than 50% when excited with light. The coating material may also have chemical compounds or ligands with moieties for bonding to target molecules and cells as well as moieties for cross-linking the coating. In the presence of reagents suitable for reacting to form capping layers, the compounds in the coating may form a capping layer on the fluorescent nanocrystal with the coating compounds operably bonded to the capping layer.

The present invention provides compositions comprising functionalized, stable, and fluorescent nanocrystals for use in nonisotopic detection systems and methods of making the same. The functionalized fluorescent nanocrystals are coated with a material comprised of a heteroaromatic compound or ligand with functional groups or moieties for imparting solubility to coated fluorescent nanocrystals in aqueous solutions. The coating material provides for functionalized fluorescent nanocrystal compositions which are water soluble, chemically stable, and emit with high efficiency light with a quantum yield of greater 10% and preferably greater than 50% when excited with light. Depending upon the ligands comprising the material coating the fluorescent nanocrystals, the functionalized fluorescent nanocrystals of the present invention may be soluble in other liquids, for example water and isopropyl alcohol mixture or liquids with surface tensions below about 80 dynes/cm, and preferably in the range from about 30-72 dynes/cm. The coating material may also have chemical compounds or ligands like isocyanates, alkyl cyanoacrylates, or alkyl phosphines with moieties for bonding to target molecules and cells as well as moieties for cross-linking the coating. In the presence of suitable reagents for example but not limited to $ZnSO_4$ and $Na_2S$, the compounds in the coating may form a capping layer on the fluorescent nanocrystal with the coating compounds operably bonded to the capping layer.

The present invention provides compositions comprising functionalized, stable, and fluorescent nanocrystals for use in nonisotopic detection systems and methods of making the same. The fluorescent nanocrystal composition is a core fluorescent nanocrystal coated with an imidazole-containing compound cross-linked with an alkyl phosphine-containing compound and complexed (e.g., by adduct formation) with an inorganic semiconductor capping layer.

The coating materials of the present invention enhance the fluorescence intensity of the core nanocrystal by several folds. Further, the functionalized, fluorescent nanocrystals according to the present invention are very soluble and stable in aqueous media at different pH levels.

The functionalized nanocrystals described in this invention display an unexpected increase in fluorescence intensity as compared to other semiconductor nanocrystal formulations known in the art. Intra-unit energy transfer between the imidazoles and the core nanocrystals may be playing a major role in the fluorescence enhancement. Other mechanisms may also account for such increase in fluorescence intensity imparted to these functionalized, fluorescent nanocrystals, may essentially include, but are not limited to, eliminating mid-band and intermediate states, passivation, charge dislocation, higher band energy condensation and resonance, modification of the bandgap of the shell semiconductor, or a combination thereof. The concept of passivation has been previously described herein. The passivating effect is due to the capping of surface Cd or Zn atoms or the like by imidazole complexation and to the capping of the counter atoms (Se or S or the like) by complexation with the alkyl phosphine-containing compounds. As to charge dislocation, imidazole and alkyl phosphine moieties present in the coating, may be susceptible to excitation by a sufficient light source. Such excitation may lead to charge transfer from the imidazole and/or alkyl phosphine moieties to the nanocrystal structure thereby resulting in an increase in fluorescence intensity, as compared to a fluorescence intensity without such internal charge transfer (internal charge transfer meaning a transfer of energy that substantially comprises a transfer within the structure of a coated nanocrystal of which the imidazole and/or alkyl phosphine are part of, as opposed to a transfer limited only to a transfer of energy between neighboring nanocrystals). As for energy condensation and fluorescence, it is anticipated that the integration of the π electrons in the imidazole and phosphine moieties with the excited electrons at the higher energy band of the core crystal is producing an energy condensation effect that yields higher level of electron-hole coupling followed by radiative relaxation. Chemical modifications of semiconductor surfaces with organic or inorganic molecules can shift the band edges of a semiconductor positive or negative (JECS 142, 2625, (1995)). Since strong surface capping and passivation of core semiconductor nanocrystals by higher band gap energy materials or organic passivators (e.g., TOPO) do not significantly enhance the fluorescence intensity of core semiconductor nanocrystals, it seems that energy condensation, energy transfer and eliminating intermediate and mid band exciton states are the major factors that underlie the fluorescence enhancement. The functionalized, fluorescent nanocrystals of the present invention are functionalized to be water-soluble and to contain one or more reactive functionalities to which a molecular probe may be operably bound. The overall structure of the functionalized, fluorescent nanocrystals of the present invention closely resembles the structure of a miniature light emitting diode (LED) where the coating materials used in this invention play the roles of hole-blocking layer and electron-transport layer.

Luminescence is the emission of light from any substance and occurs from electronically excited states. Luminescence is divided into two categories, fluorescence and phosphorescence, depending on the nature of the excited state. When the return of the excited electrons to the ground state is spin-allowed, the return is fast and this process is termed fluorescence (typically, a 10 nano second process). When the return of electrons to the ground states is spin forbidden it takes longer time (>100 ns), and the emitted light is termed phosphorescence. Luminescence efficiency means the amount of light (in candela units for example) that can be produced from a certain amount of nanocrystals using unlimited source of energy, for example beta emitter, light, recombination of injected charge carriers, or electrical current. The term quantum yield or efficiency in this case is different because it describes the ratio of energy recovery after applying certain amount of energy as photons, while, luminescence efficiency is different because it describes the full capacity of the nanocrystals (or a light source) apart from the amount of energy applied. In the practice of embodiments of the present invention either the Quantum yield the luminescence efficiency or both are increased by the coating material compositions of this invention.

In other embodiments of this invention, the ligands of functionalized fluorescent nanocrystal may increase the fluorescence efficiency (quantum yield) upon binding to the surface of the nanocrystal. In another embodiment of this invention, the ligands of the functionalized fluorescent nanocrystals may increase the fluorescence efficiency by one or more of the following mechanisms: internal energy transfer (antenna effect), energy condensation, elimination of intermediate and mid band exciton states, and surface passivation.

The above and other objects, features, and advantages of the present invention will be apparent in the following DETAILED DESCRIPTION of the invention when read in conjugation with accompanying drawings in which reference numerals denote the same or similar parts throughout the several illustrated views and embodiments.

DETAILED DESCRIPTION OF THE INVENTION

Figure 1A:
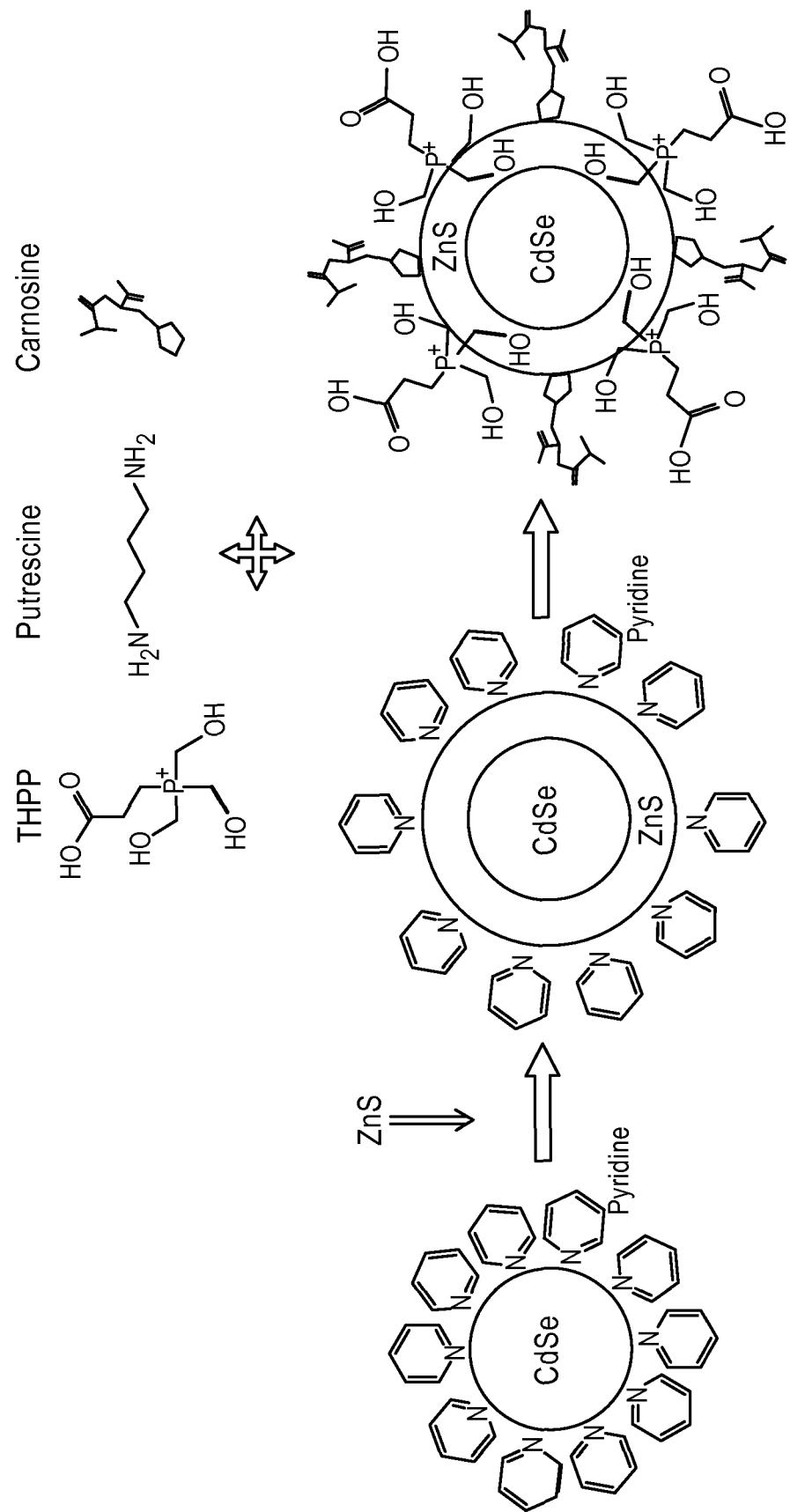
FIG. 1A is a schematic representation of the new coating system and a process for its formation.

Throughout the specification of the application, various terms are used such as "primary", "secondary", "first", "second", and the like. These terms are words of convenience in order to distinguish between different elements, and such terms are not intended to be limiting as to how the different elements may be utilized.

By the term "target molecule' is meant, for the purpose of the specification and claims to refer to a molecule of an organic or inorganic nature, the presence and/or quantity of which is being tested for; and which contains a molecular component (e.g., ligand or sequence or epitope or domain or portion or chemical group or reactive functionality or determinant, or the like) for which a molecular probe has binding specificity. The molecule may include, but is not limited to, a nucleic acid molecule, protein, glycoprotein, eukaryotic cell, prokaryotic cell, lipoprotein, peptide, carbohydrate, lipid, phospholipid, aminoglycans, chemical messenger, biological receptor, structural component, metabolic product, enzyme, antigen, drug, therapeutic, toxin, inorganic chemical, organic chemical, a substrate, and the like. The target molecule may be in vivo, in vitro, in situ, or ex vivo.

By the term "molecular probe" is meant, for purposes of the specification and claims, to mean a molecule which has binding specificity and avidity for a molecular component of, or associated with, a target molecule. In general, molecular probes are known to those skilled in the art to include, but are not limited to, lectins or fragments (or derivatives) thereof which retain binding binding function, monoclonal antibodies ("mAb", including chimeric or genetically modified monoclonal antibodies which may be preferable for administration to humans). Peptides, aptamers, and nucleic acid molecules (including but not limited to, single stranded RNA or single-stranded DNA, or single-stranded nucleic acid hybrids, oligonucleotide analogs, backbone modified oligonucleotide analogs, morpholino-based polymers), and nucleobases. The term "nucleobase" is used herein to refer to a nucleic acid moiety including, but not limited to: nucleosides (including derivatives, or functional equivalents thereof, and synthetic or modified nucleosides, and particularly, a nucleoside comprising a reactive functionality (e.g., free amino group or carboxyl group)); nucleotides (including dNTPs, ddNTPs, derivatives or functional equivalents thereof, and particularly, a nucleotide comprising a reactive functionality (e.g., free amino group or carboxyl group); acyclonucleoside triphosphates (see, e.g., U.S. Pat. No. 5,558, 991); 3'(2')-amino-modified nucleosides, 3'(2')-amino-modified nucleotides, 3'(2')-thiol-modified nucleosides, 3'(2')-thiol-modified nucleotides (see, e.g., U.S. Pat. No. 5,679, 785); alkylamino-nucleotides (see, e.g., as a chain terminator, U.S. Pat. No. 5,151,507); nucleoside thiotriphosphates (see, e.g., U.S. Pat. No. 5,187,085); and the like. The term "monoclonal antibody" is also used herein, for purposes of the specification and claims, to include immunoreactive fragments or derivatives derived from a mAb molecule, which fragments or derivatives retain all or a portion of the binding function of the whole mAb molecule. Such immunoreactive fragments or derivatives are known to those skilled in the art to include F(ab')2, Fab', Fab, Fv, scFV, Fd' and Fd fragments. Methods for producing the various fragments or derivatives from mABs are well known in the art (see, e.g., Pluckthum, 1992, Immunol. Rev. 130:152-188; for example, via pepsin digestion, papain digestion, reduction of disulfide bridges, and methods described in U.S. Pat. No. 4,642,334). Single chain antibodies can be produced as described in U.S. Pat. No. 4,946,778. The construction of chimeric antibodies is now a straightforward procedure (Adair, 1992, Immunological Reviews 130: 5-40) in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art (Adair, 1992, supra; Singer et al., 1993, J. Immunol. 150: 2844-2857). Methods for making a chimeric non-human/human mAb in general are described in detail in U.S. Pat. No. 5,736,137. Aptamers can be made using methods described in U.S. Pat. No. 5,789,157. Lectins and fragments thereof are commercially available. Oligonucleotide analogs, backbone modified oligonucleotide analogs, and morpholino-based polymers can be made using methods described in U.S. Pat. Nos. 5,969,135, and 5,596,086, U.S. Pat. Nos. 5,602,240, and 5,034,506, respectively. "Molecular probe" may also be used herein to refer to a plurality of molecules of molecular probe which may be operably bound to a functionalized, fluorescent nanocrystal.

By the terms "operably bind" and "operably bound" are meant, for purposes of the specification and claims to refer to fusion or bond or an association, of sufficient stability for the purposes of use in detection systems as described herein and standard conditions associated therewith as known in the art, formed between a combination of different molecules including, but not limited to, between a coating compound and fluorescents nanocrystal, between a coating compound and molecular probe, between different molecular probes, and between molecular probe and target molecule. A coating may comprise one or more ligands. As known to those skilled in the art, and as will be more apparent by the following embodiments, there are several methods and compositions in which two or more molecules may be operably bound utilizing reactive functionalities. Reactive functionalities include, but are not limited to, bifunctional reagents (e.g., homobifunctional or heterobifunctional), biotin, avidin, free chemical groups (e.g., thiol, or carboxyl, hydroxyl, amino, amine, sulfo, and the like), and reactive chemical groups (reactive with free chemical groups). As known to those skilled in the art, the bond may compromise, but is not limited to, one or more of: covalent, ionic, hydrogen, van der waals, and the like.

Figure 1B:
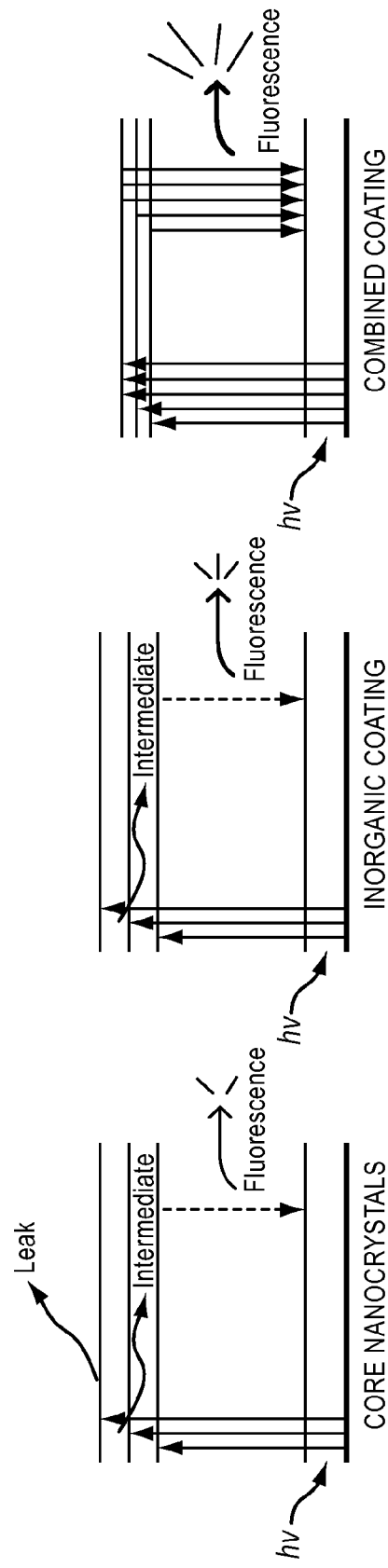
FIG. 1B is the anticipated energy change diagrams during the coating process according to the present invention.

By the term "imidazole-containing compound" is meant, for purposes of the specification and claims to refer to a heterocyclic or heteroaromatic molecule or ligand in a coating that has at least one imidazole group (e.g., imidazole ring) available for binding with the fluorescent nanocrystal or capping compound a metal such as zinc, cadmium, gallium, or other metal cation, or substrate containing such cation. In that respect, preferably at least one imidazole moiety is in a terminal position with respect to the structure of the molecule. The imidazole containing compound operably bonds to the fluorescent nanocrystal through the imidazole ring which comprises delocalized molecular orbitals. Generally, imidazole ring nitrogens serve as coordinating ligand, as illustrated in FIG. 1, to operably bind a metal ion such as zinc or cadmium. In a preferred embodiment, the imidazole-containing compound comprises additional reactive functionalities such as an amino acid, or two or more amino acids joined together (e.g., known in the art as "peptidyl" or "oligopeptide"), which may include, but is not limited to, histidine, carnosine, anserine, baleine, homocarnosine, histidylphenylalanine, cyclo-histidylphenylalanine, 5-amino-4-imidazolecarboxamide, histidylleucine, 2-mercaptoimidazole, boc-histidine hydrazide, histidinol, 1-methylhistidine, 3-methylhistidine, imidazolysine, imidazole-containing ornithine (e.g., 5-methylimidazolone), imidazole-containing alanine (e.g., (beta)-(2-imidazolyl)-L(alpha) alanine), carcinine, histamine, and the like. These histidine-based molecules or imidazole-containing amino acids, may be synthesized using methods known in the art (see, e.g., Stankova et al., 1999, J. Peptide Sci. 5: 392-398, the disclosure of which is herein incorporated by reference).

By the term "amino acid" is meant, as known in the art and for purposes of the specification and claims, to refer to a compound or ligand containing at least one amino group and at least one carboxyl group. As known in the art, an amino group may occur at the position adjacent to a carboxyl group, or may occur at any location, for example β and γ amino acids, along the amino acid molecule. In addition to at least one imidazole moiety, the amino acid may further comprise one or more additional reactive functionalities (e.g., amino, thiol, carboxyl, carboxamide, etc.). The amino acid may be a naturally occurring amino acid, a synthetic amino acid, a modified amino acid, an amino acid derivative, an amino acid precursor, in D (dextro) form, or in L (levo) form. Examples of derivatives may include, but are not limited to, an n-methylated derivative, amide, or ester, as known in the art. Consistent with the functionality of the amino acid, it acts as a coating for the fluorescent nanocrystals and may impart water-solubility, buffer sufficiently in a pH range between about pH 6 and about pH 10, functions as a coat which can increase fluorescence intensity, and has one or more reactive functionalities that may be used to operably bind at least one molecular probe. An amino acid of the aforementioned amino acids may be used in a preferred embodiment, and a preferred amino acid may be used separately in the composition of the present invention to the exclusion of amino acids other than the preferred amino acid. Carnosine (alanyl histidine) is a preferred histidine-based or imidazole-containing compound for coating the functionalized, fluorescent nanocrystals according to the present invention.

Other molecules or ligands may be used in place of imidazole in the practice of this invention. These ligands, (such as those disclosed in Cotton and Wilkinson, $3^{rd}$ Ed, Chapter 21) may operably bond to fluorescent nanocrystal surfaces, coordinate or chelate metal ions and preferably have Lewis base properties and or conjugated moieties. These molecules may also have moieties for imparting solubility or wettability in aqueous solutions to fluorescent nanocrystals coated with them. The molecules may also have chemical moieties for bonding to target molecules and cells as well as moieties for cross-linking them. In the presence of reagents suitable reagents like $ZnSO_4$ and $Na_2S$, these molecules or compounds may react to form a capping layer on the fluorescent nanocrystal with the molecules operably bonded to the capping layer. The molecules may also operably bond to atoms or ions on the surface of the nanocrystal. The result of using these molecules or compounds is a functionalized nanocrystal with enhanced luminescence, water solubility and chemical stability. These molecules or compounds have at least one Lewis acid and or a conjugated moiety in a terminal position with respect to the structure of the molecule. Generally, cyclic or linear unsaturated compounds with resonating electrons or with resonating heterogeneous rings frequently serve as coordinating ligand to operably bind a metal ion such as zinc or mercury, or cadmium. The ligand bonds to the fluorescent nanocrystal with its moiety that comprises delocalized molecular orbitals as illustrated in FIG. 1. These molecules or compounds may comprise a heterogeneous ring, or two or more joined together, examples include, but are not limited to, thiazole, thiazole derivatives, oxazole, oxazole derivatives, pyrrole, pyrrole derivatives including doped or undoped polypyrrole, thiophene, thiophene derivatives including doped or undoped poly-thiophenes, furan, furan derivatives, pyridine, pyridine derivatives, pyrimidine, pyrimidine derivatives, pyrazine, pyrazine derivatives, triazine, triazine derivatives, triazole, triazole derivatives, phthalocyanine, phthalocyanine derivatives, porphyrin, porphyrin derivatives. These compounds may comprise unsaturated (olefin) hydrocarbons or their amine, phosphorus, oxygen derivatives, which may include but are not limited to acetylene, propyne, and allene. It is preferred that the molecule have sufficient p-electron density to engage in adduct formation or resonance on the surface of the semiconductor nanocrystal.

By the term "alkyl phosphine cross-linking compound" is meant, for purposes of the specification and claims to refer to a molecule or ligand that has at least one phosphine group available for binding or chelating a non metal such as Se, S or other non metals, or substrate containing such atoms, and has at least one functional group (e.g., hydroxyl, amino, thiol, carboxyl, carboxamide, etc) with ability to react with neighboring molecules. In that respect, preferably at least one phosphine moiety is in a terminal position with respect to the structure of the molecule as illustrated in FIG. 1. Generally, phosphine moieties frequently serve as coordinating ligand to operably bind with the fluorescent nanocrystal or capping compound a non metal or ion such as Se or S. In a preferred embodiment, the alkyl phosphine-containing compound comprises a phosphine group, or two or more phosphine groups joined together (e.g., in a polymeric form), which may include, but is not limited to, hydroxymethylphosphine compounds, and the like. Alkyl phosphine-containing compounds may be synthesized using methods known in the art (see, e.g., Tsiavaliaris et al., 2001, Synlett. 3: 391-393, Hoffman et al, 2001, Bioconjug Chem 12: 354-363, U.S. Pat. No. 5,948, 386). As known in the art, an alkyl phosphine-containing compound may further comprise one or more additional reactive functionalities (e.g., hydroxyl, amino, thiol, carboxyl, carboxamide, etc.). Examples of derivatives may include, but are not limited to, a hydroxy methyl phosphine derivative, amide, or ester, as known in the art, and where consistent with the functions of the alkyl phosphine as a coating as described herein (e.g., imparts water-solubility, buffers sufficiently in a pH range between about pH 6 and about pH 10, functions as a coat and cross-linker which can increase stability and fluorescence intensity, and has one or more reactive functionalities that may be used to operably bind molecular probe). An alkyl phosphine of the aforementioned derivatives may be used in a preferred embodiment, and a preferred alkylphosphine may be used separately in the composition of the present invention to the exclusion of alkyl phosphines other than the preferred alkyl phosphine. Tris(hydroxy methyl) phosphine and beta-[Tris(hydroxymethyl)phosphino]propionic acid are particularly preferred alkyl phosphine-containing compound for coating, stabilizing and functionalizing fluorescent nanocrystals according to the present invention. Also known in the art is that cross-linked alkyl phosphine-containing compounds have additional ability to operably bind to metal atoms and/or ions such as zinc and cadmium. In this respect functionalized isocyanates or alkyl cyanoacrylates may also be useful for cross-linking ligands and adduct formation with fluorescent nanocrystals in the practice of this invention.

The nanocrystal coated with the coating material of the present invention may further comprise an additional layer on the surface of the coating material. The moieties of the layer may be organic or inorganic and provide chemical compatibility, reactivity, or solubility with a fluid or suspension media. For example, additional amino acids like arginine may be coupled to the imidazole-containing group in the coating material, or short chain polymer or peptide sequences like arginine-glycine-serine, with the serine hydroxyl moiety interacting with the suspending medium, may be used in the practice if this invention. Amino acids and other such groups will have an affinity for the amino acid portion of the imidazole containing group of the coating material and may be reacted with them using standard coupling reactions.

By the term "fluorescent nanocrystals" is meant, for purposes of the specification and claims to refer to nano-crystals comprising semiconductor nanocrystals or doped metal oxide nanocrystals, to which may be operably bound various ligands including histidine-based or imidazole-containing compounds and phosphonium compounds. "Semiconductor nanocrystals" is meant, for purposes of the specification and claims to refer to quantum dots (also known as crystallite semiconductors) comprised of a core comprised of at least one of a Group II-VI semiconductor material (of which ZnS, HgS, and CdSe are illustrative examples), or a Group III-V semiconductor material (of which GaAs is an illustrative example), or a Group IV semiconductor nanocrystal, or a combination thereof. These core semiconductor nanocrystals may further comprise and be passivated with a "shell" or capping layer of material uniformly deposited on the core. The capping layer material may be comprised of an inorganic material with a higher band gap than the core nanocrystal. Inorganic materials typically used to passivate CdX (X=S, Se, Te) core nanocrystals are preferably comprised of YZ where "Y" is Cd, Hg, or Zn and "Z" is S, Se, or Te. Core CdX nanocrystals with a YZ shell can be made by the methods in: (see, e.g., Danek et al., 1996, Chem. Mater. 8: 173-179; Dabbousi et al., 1997, J. Phys. Chem. B 101: 9463; Rodriguez-Viejo et al., 1997, Appl. Phys. Lett. 70: 2132-2134; Peng et al., 1997, J. Am. Chem. Soc. 119: 7019-7029; 1996, Phys. Review B. 53: 16338-16346; the disclosures of which are hereby incorporated by reference). The core nanocrystal with the capping layer may include 0 to about 5.3 monolayers of the capping semiconductor material, preferably it includes less than about 1 monolayer of the capping semiconductor material. As known to those skilled in the art, the size of the core of the semiconductor nanocrystal correlates with the spectral range of emission. Table 1 is an illustrative example for CdSe.

TABLE 1

| Color | Nanocrystal Size Range (nm) | Peak Emission Range (nm) |
| --- | --- | --- |
| Blue | 2.1 to 2.9 | 436 to 500 |
| Green | 2.9 to 4.7 | 500 to 575 |
| Yellow | 4.7 to 5.0 | 575 to 592 |
| Orange | 5.0 to 6.1 | 592 to 620 |
| Red | 6.1 to 10.2 | 620 to 650 |

In a preferred embodiment, the semiconductor nanocrystals are produced using a continuous flow process and system (see, U.S. Pat. No. 6,179,912), and may have a particle size that varies by less than +/−10% in the average particle size (as measured by diameter) in the range of approximately 1 nanometer (nm) to approximately 20 nm. Semiconductor nanocrystals useful in the practice of various embodiments of this invention may also be characterized in that the dimensions of the nanocrystals are comparable or smaller than their bulk exciton diameter so that they exhibit size dependent optoelectronic properties.

By the term "doped metal oxide nanocrystals" is meant, for purposes of the specification and claims to refer to nanocrystals comprised of: a metal oxide, and a dopant comprised of one or more rare earth elements. For example, metal oxides include, but are not limited to yttrium oxide ($Y_2O_3$), zirconium oxide ($ZrO_2$), zinc oxide (ZnO), copper oxide (CuO or $Cu_2O$), gadolinium oxide ($Gd_2O_3$), praseodymium oxide ($Pr_2O_3$), lanthanum oxide ($La_2O_3$), and alloys thereof. Doped metal oxide nanocrystals with rare earth elements may include but are not limited to oxides of elements selected from the Lanthanide series such as europium (Eu), cerium (Ce), neodymium (Nd), samarium (Sm), terbium (Tb), gadolinium (Gd), holmium (Ho), thulium (Tm), and alloys containing these elements. As known to those skilled in the art, depending on the dopant, an energized doped metal oxide nanocrystal is capable of emitting light of a particular color. Thus, the nature of the rare earth or rare earths are selected in consequence to the color sought to be imparted (emitted) by a doped metal oxide nanocrystal used to label a microsphere according to the present invention. A given rare earth or rare earth metal combination in a doped metal oxide has a given color. By adjusting the nature of the dopant and or the concentration of the dopant, the doped metal oxide nanocrystals may emit (with a narrow emission peak) a color over an entire range of colors. For example, the emission color and brightness (e.g., intensity) of a doped metal oxide nanocrystal comprising $Y_2O_3$:Eu may depend on the concentration of the Eu dopant; e.g., emission color may shift from yellow to red with increasing Eu concentration. For purposes of illustration only, representative colors which may be provided by various dopants in $Y_2O_3$ are listed in Table 2.

TABLE 2

| Fluorescent Color | Dopant |
| --- | --- |
| Blue | Thulium |
| Blue | Cerium |
| Yellow-green | Terbium |
| Green | Holmium |
| Green | Erbium |
| Red | Europium |
| Reddish | Samarium |
| Orange | Neodymium |
| Yellow | Dysprosium |
| White | Praseodymium |
| Orange-yellow | Europium + terbium |
| Orange-red | Europium + samarium |

Methods for making doped metal oxide nanocrystals are known to include, but are not limited to a sol-gel process (see, e.g., U.S. Pat. No. 5,637,258), and an organometallic reaction. As will be apparent to one skilled in the art, the dopant (e.g., one or more rare earth elements) are incorporated into the doped metal oxide nanocrystal in a sufficient amount to permit the doped metal oxide nanocrystal to be put to practical use in fluorescence detection. Without enough dopant, the doped metal oxide nanocrystal would fail to emit sufficient detectable fluorescence, too much dopant which would cause reduced fluorescence due to concentration quenching. In a preferred embodiment, the amount of dopant in a doped metal oxide nanocrystal is a molar amount in the doped metal oxide nanocrystal selected in the range of from about 0.1% to about 25%. Doped metal oxide nanocrystals may be excited with a single excitation light source resulting in a detectable fluorescence emission of high quantum yield (e.g., a single nanocrystal having at a fluorescence intensity that may be a log or more greater than that a molecule of a conventional fluorescent dye) and with a discrete fluorescence peak. Typically, doped metal oxide nanocrystals have a substantially uniform size of less than 200 Angstroms, and preferably have a substantially uniform size in the range of sizes of from about 1 nm to about 5 nm. In one embodiment, the doped metal oxide nanocrystals are comprised of metal oxides doped with one or more rare earth elements, wherein the dopant comprising the rare earth element is capable of being excited (e.g., with ultraviolet light) to produce a narrow spectrum of fluorescence emission. In another embodiment, the doped metal oxide has both fluorescent properties (when excited with an excitation light source) and magnetic properties; thus, a polymeric microsphere (which is substantially nonmagnetic) embedded or labeled with a plurality of fluorescent nanocrystals (comprising doped metal oxide nanocrystals which are magnetic material) may form fluorescent microspheres which are magnetic.

By the term "functionalized fluorescent nanocrystals" is meant, for purposes of the specification and claims to refer to fluorescent nanocrystals which are coated. The coating may include but is not limited to cations, ligands, molecules with conjugated moieties as well as lyophilic and bonding moieties, cross linking molecules, and molecular probes. An example of such a material coating is an imidazole-containing compound and alkyl phosphine containing compound.

Functionalized fluorescent nanocrystals according to the present invention are soluble in aqueous solutions and other fluids depending upon the ligands comprising the material coating. For example, they may be soluble in water, water and isopropyl alcohol mixtures or liquids with surface tensions below about 80 dynes/cm, and preferably in the range from about 30-73 dynes/cm. The solvent or solvent mixture used to solublize or suspend the functionalized nanocrystals may have a surface energy which is about the same as the surface energy of the particular coating material of the functionalized nanocrystal. The surface energy of coating will vary with the molecular properties and amount of the ligands in the coating material; preferably the moiety of the coating material is compatible, soluble and chemically stable, with the fluids it is contacted with. Chemically stable moieties of the coating material maintain the fluorescent emission intensity over time as required by the application of the functionalized fluorescent nanocrystals. The functionalized nanocrystals (FNC) of the present invention were soluble in water, mixtures of water and glycerol (50%), water and ethanol (10%), water and methanol (50%; ~35 dynes/cm), water and DMSO (50%), water and polyethylene glycol 200 (50%), and water and isopropyl alcohol (50%). The FNC were also soluble in 100% of glycerol, isopropyl alcohol particularly after adding other solvents to isopropyl alcohol. The functionalized fluorescent may operably bond molecular probes and target molecules, have increased fluorescence intensity when excited by a suitable excitation source; and may further demonstrate chemical stability in a pH range of from about pH 6.0 to about 10.5. Preferred functionalized, fluorescent nanocrystals may be produced, and used in the method and system as according to present invention, to the exclusion of functionalized, fluorescent nanocrystals other than the preferred functionalized, fluorescent nanocrystals.

In a preferred embodiment to form the functionalized, fluorescent nanocrystals according to the present invention, a core nanocrystal may be coated by the co-precipitation of a compound comprising a metal cation (e.g., for forming a semiconductor material, preferably, with a high bad gap energy, as known in the art; "shell") operably bound to an imidazole-containing compound and to an alkyl phosphine-containing compound, wherein the coat is uniformly deposited over the outer surface of the nanocrystal core. This is both functionally and fundamentally different than using zinc-histidine as nucleation centers for growing core nanocrystals (see, Kho et al., 2000, Biochem. Biophys. Res. Commun. 272: 29-35). As an example of this preferred embodiment, a Group II-VI semiconductor core may be capped with a Group II-VI semiconductor shell (e.g., a ZnS or CdSe core may be coated with a shell comprised of YZ wherein Y is Cd or Zn, and Z is S, or Se) and further coated with an imidazole-containing compound cross-linked with an alkyl phosphine-containing compound. Preferably both the semiconductor shell and imidazole-containing compound cross linked with the alkyl phosphine-containing compound coating passivate the outer surface of the core nanocrystal and result in enhanced fluorescence.

In another embodiment, a core/shell nanocrystal (e.g., CdX core/YZ shell) produced using methods standard in the art is coated with a metal cation (preferably capable of forming a semiconductor material, like ZnS, with a high band gap energy) operably bound to an imidazole-containing compound cross-linked with an alkyl phosphine-containing compound. The coating is uniformly deposited over the outer surface of the core/shell nanocrystal.

In another embodiment, a fluorescent nanocrystal may be coated with a material that has an imidazole-containing compound cross-linked with alkyl phosphine-containing compound that produces the functionalized fluorescent nanocrystals according to the present invention. The functionalized fluorescent nanocrystal composition may luminescence with an efficiency of greater than about 10-fold of that of non coated fluorescent nanocrystals when irradiated with light or other source of excitation.

In yet another embodiment, a fluorescent nanocrystal may be coated with a coating comprising an imidazole-containing compound and alkyl phosphine-containing compound.

In another embodiment, the functionalized, fluorescent nanocrystals according to the present invention further comprises chemical or physical cross-linking of the coating material comprising imidazole-containing compound and alkyl phosphine-containing compound to promote further stabilization of the coat of the functionalized, fluorescent nanocrystal. Chemical cross-linking can be achieved by using methods and reagents known in the art which may include, but are not limited to, formaldehyde, glutaraldehyde, acrolein, 1,6-hexane-bis-vinylsulfone, putrescine, alkyl diamines, and other organic triamines or polyamines. Physical cross-linking and/or curing can also be achieved by using methods known in the art which may include, but are not limited to, ultraviolet irradiation, microwave treatment, heat treatment, and radiation.

Excitation sources suitable for characterizing the functionalized fluorescent nanocrystals of this invention include but are not limited to polychromatic ultraviolet and visible lamps, substantially monochromatic sources light, polarized light, beta emitters including but not limited to $^{33}P$, $^{125}I$, and $^{3}H$. Sources of light may include low, medium, and high pressure lamps as well as lasers. Electric current and electron bombardment of the nanocrystals may also be used for excitation. Suitable detectors may include but are not limited to visual detection, photodiodes, photomultipliers, heat detectors and charge coupled device detectors (CCDs); detectors may also include the use of polarizing filters.

The functionalized fluorescent nanocrystal prepared by the methods and materials of embodiments of the present invention may be characterized by luminescent efficiency or quanum yield. For example, fluorescent nanocrystals that have been coated with an imidazole containing or ligand with delocalized electrons operably bonded to the nanocrystal may be excited with a light source and the number of photons from the fluorescence measured to characterize the Quantum Yield of the complex. Alternatively, the coated fluorescent nanocrystals may be connected to anodes and cathodes as know to those skilled in the art, and luminescent output based on injected charge used to characterize the luminescent efficiency of the functionalized fluorescent nanocrystal. Adjustment to the amount and type of imidazole containing ligand, phosphine cross linker, cross linker, or other parameters may be made and used to change the luminescent properties of the coated crystals.

An effective amount of a coating is an amount of coating where the steric interactions of the coating molecules (determined by size, intermolecular bonding, cross linking, and operable bonding to target molecules) and their electronic interaction with the fluorescent nanocrystal are such that the functionalized fluorescent nanocrystal has a quantum yield in excess of 10% and preferably in excess of 50% when excited with light.

The present invention provides compositions comprising functionalized, fluorescent nanocrystals which can be used in a variety of types of fluorescence-based detection systems. Examples include, but are not limited to, building three dimensional dendrimers which function to generate and significantly amplify a detectable signal (thereby considerably improving the sensitivity of a non-isotopic detection system; see, e.g., U.S. Pat. No. 6,261,779, the disclosure of which is herein incorporated by reference). Another example is to use the functionalized fluorescent nanocrystals of the present invention to label nucleobases and provide fluorescence-labeled nucleobases for nucleic acid strand synthesis or nucleic acid sequence determination (see, e.g., U.S. Pat. No. 6,221, 602, the disclosure of which is herein incorporated by reference). Another example is to use the functionalized fluorescent nanocrystals of the present invention to make fluorescent microspheres (e.g., beads) by either embedding microspheres with and/or to operably bind microspheres to functionalized fluorescent nanocrystals. Another example is to use the functionalized fluorescent nanocrystals of the present invention in fluorescent ink compositions suitable for printing on substrates. In this example, the functionalized fluorescent nanocrystal ink composition is applied to a substrate in an identifiable code pattern and is then excited with a suitable for purposes of identification, verification, security, or ornamentation.

As will be apparent to one skilled in the art, the functionalized, fluorescent nanocrystals according to the present invention may be used in a detection system that may include, but is not limited to, one or more of: an affinity assay (e.g., immunoassay such as an ELISA), fluorescent staining (e.g., immunofluorescent staining on a glass slide, fluorescent in situ hybridization, and the like), flow cytometry, cell imaging-based detection assays (e.g., cell-based ELISA or "cELISA", image cytometry, cells grown in standard high density microarrays), microarray-based detection assays (e.g., oligonucleotide scanning arrays, combinational DNA arrays, microchips containing arrays of nucleic acid molecules or protein molecules, multi-channel microchip electrophoresis, and the like), microfluidics-based detection assays (e.g., "lab-on-a-chip" systems as known in the art), fluorescence-based biosensors (see, e.g., Trends in Biotech. 16: 135-140, 1999), nucleic acid sequencing, nucleic acid hybridization, nucleic acid synthesis or amplification, manufacturing of light emitting diodes, identification verification (e.g., identification card or bank card), fluorescent bead-based detection assays, molecular sorting (e.g., cell sorting by flow cytometry), and the like.

This example illustrates embodiments of a process of making the functionalized, fluorescent nanocrystals according to the present invention. For this and subsequent examples, semiconductor nanocrystals comprising core nanocrystals were produced using a continuous flow process as described in the U.S. Pat. No. 6,179,912. The following parameters were used to produce nanocrystals of cadmium selenide (CdSe): 10 g TOPO; 18.9 ul of Me$_2$Cd (dimethyl cadmium; e.g., $2.63 \times 10^{-4}$ moles of Cd); 198.9 ul of TOPSe (1M solution of Se in TOP; e.g., $1.989 \times 10^{-4}$ moles of Se); 4.5 ml of TOP; nucleation temperature (Tn) of 300 C; growth temperature (Tg) of 280° C.; and flow rate of 0.1 ml/min. The resulting CdSe nanocrystals displayed fluorescence at a wavelength of 578 nm, with an excitation wavelength of 410 nm, and a narrow bandwidth at half height of about 29 nm.

The process of making functionalized, fluorescent nanocrystals may comprise contacting fluorescent nanocrystals, for example CdSe, ZnS or (CdSe)ZnS with a solution comprising a ligand or an imidazole-containing compound and then with a solution comprising another ligand such as an alkyl phosphine-containing compound. When metal ions like $Cd^{+2}$ or $Zn^{+2}$ are present in solution or on the fluorescent nanocrystal, the ligand or the imidazole-containing compound operably binds to the metal cation and the alkyl phosphine-containing compound operably binds to the counterpart non metal element (e.g., S, Se, or the like) in producing a coat over the fluorescent nanocrystals in forming functionalized, fluorescent nanocrystals.

As previously described, the fluorescent nanocrystals which are coated by the process may comprise core semiconductor nanocrystals, core/shell semiconductor nanocrystals, doped metal oxide nanocrystals, or a combination thereof. With respect to metal cations, ligands or other imidazole-containing compounds have been reported to operably bind metal ions which may include, but are not limited to one or more of, $Zn^{2+}$, $Cu^{2+}$, $Fe^{2+}$, $Hg^{+2}$, $Ni^{2+}$, $Cd^{2+}$, $Co^{2+}$, and the like. With respect to non metal counter part anions, alkyl phosphine-containing compounds have been reported to operably bind to non metal elements which may include, but are not limited to one or more of, O, S, Se, Te, Po and the like.

For example, core fluorescent nanocrystals are prepared and firstly coated by an inorganic layer of ZnS according to methods known in the art to form core/shell type nanocrystals, and then the core/shell type nanocrystals are coated by a second coating solution comprising a ligand or an imidazole-containing compound and then with a solution comprising an alkyl phosphine-containing compound. The ligand or imidazole-containing compound operably binds to the metal cation if present (e.g., $Cd^{+2}$, $Zn^{+2}$ or the like) and the alkyl phosphine-containing compound operably binds to the counterpart non metal element (e.g., S, Se, or the like) in producing a coat over the fluorescent nanocrystals in forming functionalized, fluorescent nanocrystals. As a general guideline, the core/shell nanocrystals coating process may comprise inclusion of components comprising, per milligram of fluorescent nanocrystals: ligands or an imidazole-containing compound in an amount ranging from about 0.25 mmole to about 2.5 mmole; alkyl phosphine-containing cross-linker in an amount ranging from about 0.25 mmole to about 2.5 mmole; and a polyamine in an amount ranging from about 0 mmole to about 2.5 mmole. As apparent to one skilled in the art, the amount of each individual component may vary depending on the particular ligand or imidazole-containing compound used, the alkyl phosphine-containing compound used, the nature (e.g., chemical composition) of fluorescent nanocrystals to be functionalized, the nature of the surface of the fluorescent nanocrystals to be coated, the ratio of other components in the coating process, and the pH of the buffer system used in the coating process.

In one embodiment of the coating process may be monitored by the emission of the fluorescent nanocrystals during the coating process. Reaction conditions such as time, temperature and concentration of reagents may be adjusted according to the emission of excited functionalized fluorescent nanocrystals during the process. A threshold emission intensity may be chosen to indicate a desired state of the coating process. For example, the coating process may continue until the emission from the fluorescent nanocrystals during the process is at least the intensity of the threshold value.

For example, a 30 mM carnosine (imidazole containing compound) solution in a 1 M CAPSO buffer (3-(Cyclohexylamino)-2-hydroxy-1-propanesulfonic acid, sodium salt, pH 9.6) was prepared. Other suitable buffers known in the art which provide buffering in a range of from about pH 8.0 to about pH 11, may be used in place of the CAPSO buffer (e.g., a sodium carbonate buffer, TAPS buffer (N-tris (hydroxymethyl)methyl-3-aminopropanesulfonic acid), and the like). To 10 ml of the carnosine solution was added 0.5 to 3 mg of CdSe nanocrystals (core crystals) suspended in a minimal volume (e.g., from about 60 ul to about 200 ul) of organic solvent (e.g., chloroform or pyridine). After mixing, and incubation for about 1 hr at room temperature, the organic phase was discarded Then to the aqueous phase was added 1.2 ml of 60 mM THPP (beta-[Tris(hydroxymethyl)phosphino]propioninc acid, alkyl phosphine-containing cross-linker). The temperature of the reactions may be modified as would be known to those skilled in the art to affect the coating process. After one hour of gentle mixing, 100 ul of 1M putrescine (polyamine) was added and mixed for additional hour. The cycle of the addition of THPP and putrescine was repeated three to four times. The final solution was treated with formaldehyde at 100 mM final concentration for about 1 hour period. The functionalized, fluorescent nanocrystals were then purified. Suitable methods of purification include but are not limited to size exclusion chromatography, dialysis, centrifugation, and a combination these methods. For example the solution comprising functionalized, fluorescent nanocrystals was dialyzed against a suitable buffer such like PBS (phosphate buffered saline) using 3000 KD MCO dialysis membranes.

The process for making the functionalized, fluorescent nanocrystals was repeated and the relative amounts of each component were varied. The resultant functionalized, fluorescent nanocrystals were characterized by: stability in aqueous solutions in a pH range of about 6 to about 10, with optimal stability in the range of from about pH 7 to about pH 9; available reactive functionalities on the surface of the functionalized, fluorescent nanocrystals (in this case, carboxyl groups) to which molecular probe may be operably bound; and fluorescence intensity. There are two measures of stability which may be used; the first, is decay in fluorescence intensity over time to a threshold of the initial value etc. Most stable crystals decay 1% in 24 hours, least stable decay 25% in 24 hours. The second measure of stability is the physical stability were there is no change in solubility, aggregation, cloudiness, or phase separation, stability toward repeated centrifugation and filtration, and toward dialysis and electrophoresis. From these formulation studies, a preferred ratio of components that showed optimal properties of fluorescence and stability (in an aqueous environment and at a wide pH range) comprises: 1 to 2 mg of core/shell nanocrystals (e.g., CdSe/ZnS); 0.35 mmole carnosine; 0.15 mmole THPP; 0.15 mmole putrescine, and 1 mmole formaldehyde.

Figure 2:
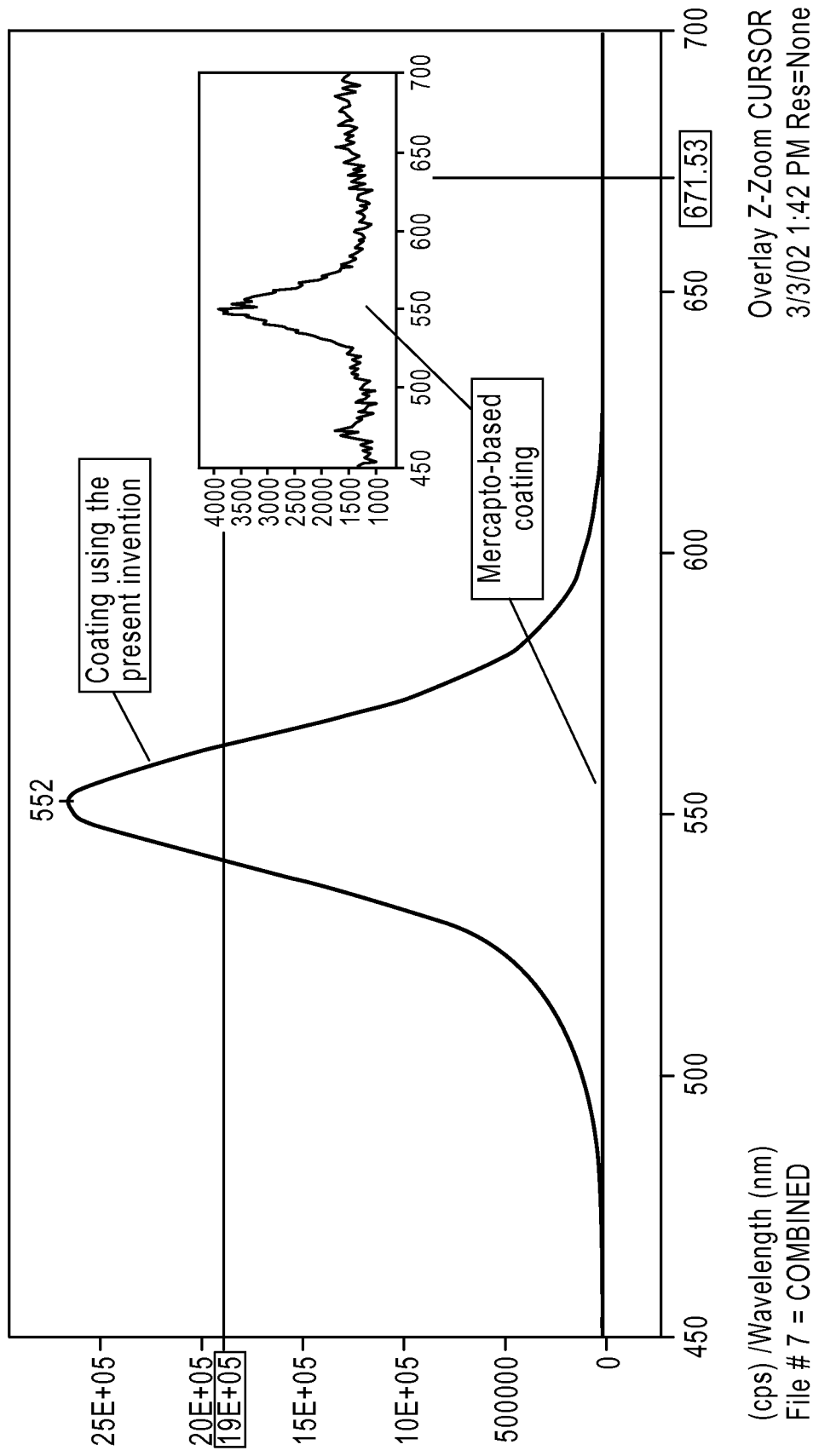
FIG. 2 is a graph showing a comparison of emission peaks of functionalized fluorescent nanocrystals of the present invention and mercapto-based functionalized nanocrystals.
Figure 3:
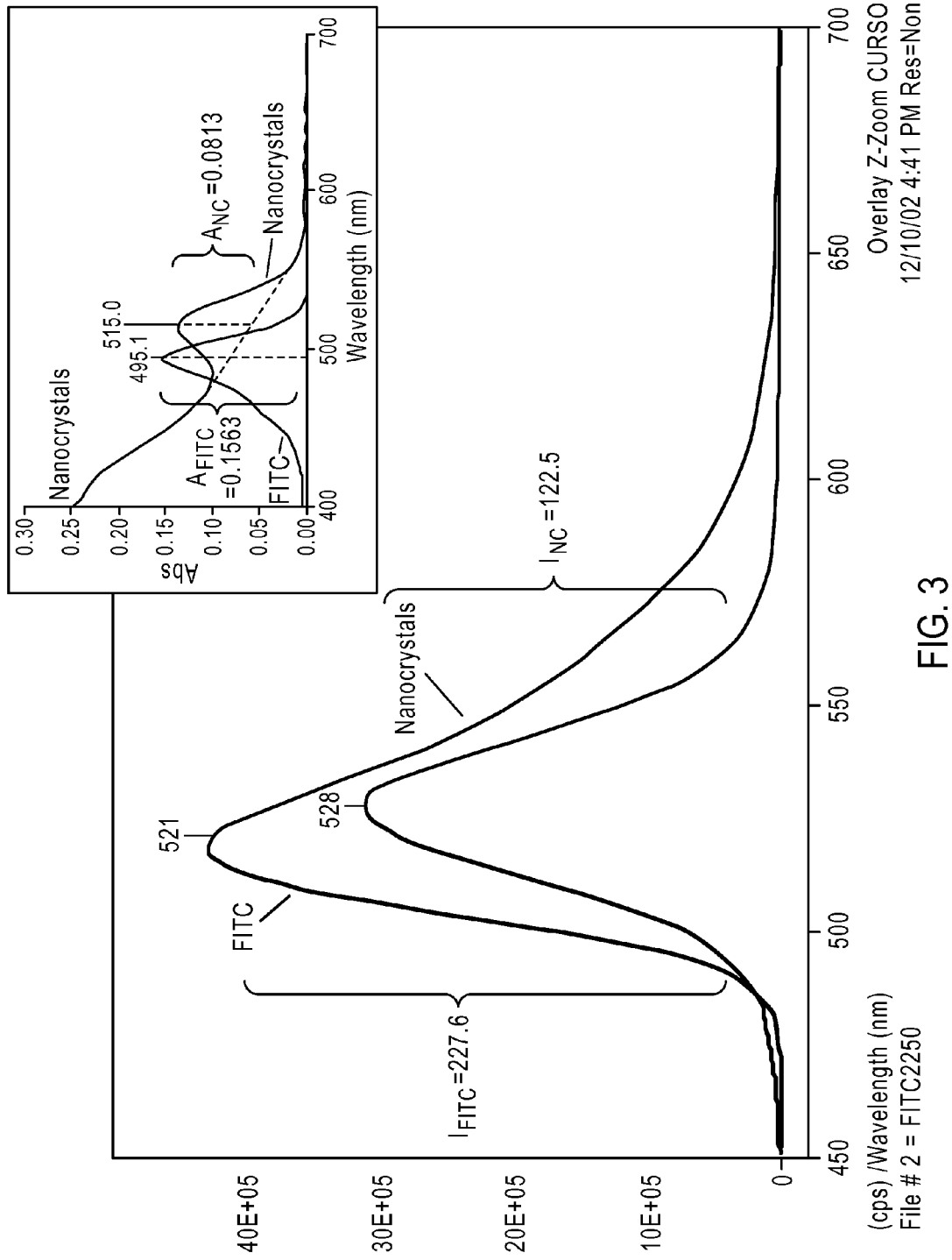
FIG. 3 is a comparison of UV and fluorescence spectra and quantum yield for fluorescein isothiocyanate (FITC) and functionalized fluorescent nanocrystals of an embodiment of the present invention. Quantum yield (QY) value of the functionalized nanocrystals was determined relative to FITC (QY=0.75~0.95) in sodium borate buffer (50 mM, pH 9.0) using the equation: QYNC=QYFITC (INC/IFITC) (AFITC/ANC) $(n/n')^2$, where, INC and IFITC are the integrated fluorescence intensity of nanocrystals and FITC, respectively; and ANC and AFITC are the UV absorbance maxima at excitation for nanocrystals and FITC respectively; and n and n' are the refractive indices of the solvents (sodium borate for both samples). According to the above equation the QYNC=0.73~1.

These functionalized fluorescent nanocrystals showed unexpected enhancement of fluorescence intensity comprising at least 50 fold to as much as about 1100 fold or more (see, e.g., FIG. 2 and inset of FIG. 2), when compared to the fluorescence intensity of functionalized fluorescent nanocrystals known in the art (e.g., CdX/YZ fluorescent nanocrystals in organic solvent or CdX/YZ fluorescent nanocrystals capped with mercapto-based compound) (see, e.g., FIG. 2). The characteristic spectral emission of the coated fluorescent nanocrystal is enhanced by the coating material. The comparison of fluorescence intensity was made by comparison to an equivalent amount of fluorescent nanocrystals made using core/shell nanocrystals from the same preparation; excitation with the same excitation light source (e.g., 410 nm); and detection using the same detection system.

In this example, provided is another embodiment of process of making functionalized, fluorescent nanocrystals by coating fluorescent nanocrystals with a coating comprising histidine as a ligand or imidazole-containing compound. As a general guideline, the core/shell nanocrystals coating process may comprise inclusion of components comprising, per milligram of fluorescent nanocrystals: a ligand or imidazole-containing compound in an amount ranging from about 0.25 mmole to about 2.5 mmole; alkyl phosphine-containing cross-linker in an amount ranging from about 0.25 mmole to about 2.5 mmole; and a polyamine in an amount ranging from about 0 mmole to about 2.5 mmole. As apparent to one skilled in the art, the amount of each individual component may vary depending on the particular ligand or imidazole-containing compound used, the alkyl phosphine-containing compound used, the nature (e.g., chemical composition) of fluorescent nanocrystals to be functionalized, the nature of the surface of the fluorescent nanocrystals to be coated, the ratio of other components in the coating process, and the pH of the buffer system used in the coating process.

For example, prepared was a 30 mM histidine (imidazole containing compound) solution in a 1 M CAPSO buffer (3-(Cyclohexylamino)-2-hydroxy-1-propanesulfonic acid, sodium salt, pH 9.6). Other suitable buffers known in the art may be used. To 10 ml of the histidine solution was added 0.5 to 3 mg of CdSe nanocrystals (core crystals) suspended in a minimal volume (e.g., from about 60 ul to about 200 ul) of organic solvent (e.g., chloroform or pyridine). After mixing, and incubation for about 1 hr at room temperature, the organic phase was discarded. Then to the mixture was added 1.2 ml of 60 mM THPP (beta-[Tris(hydroxymethyl)phosphino]propioninc acid, alkyl phosphine-containing cross-linker). After one hour of gentle mixing, 100 ul of 1M putrescine (polyamine) was added and mixed for additional hour. The cycle of the addition of THPP and putrescine was repeated three to four times. The final solution was treated with formaldehyde at 100 mM final concentration for about 1 hour period. The functionalized, fluorescent nanocrystals were then purified as previously described.

This process for making the functionalized, fluorescent nanocrystals was repeated, whereby the relative amounts of each component were varied. The resultant functionalized, fluorescent nanocrystals were characterized by: stability in aqueous solutions of the general pH range of about 6 to about 10, with optimal stability in the range of from about pH 7 to about pH 9; availability of reactive functionalities on the surface of the functionalized, fluorescent nanocrystals (in this case, carboxyl groups) to which molecular probe may be operably bound; and fluorescence intensity. From these formulation studies, a preferred ratio of components that showed optimal properties of fluorescence and stability (in an aqueous environment and at a wide pH range) comprises: 1 to 2 mg of core/shell nanocrystals (e.g., CdSe/ZnS); 0.35 mmole histidine; 0.15 mmole THPP; 0.15 mmole putrescine, and 1 mmole formaldehyde.

These functionalized fluorescent nanocrystals showed unexpected enhancement of fluorescence intensity, about 50 fold to as much as about 1100 fold or more, when compared to fluorescence intensity of functionalized fluorescent nanocrystals known in the art (e.g., CdX/YZ fluorescent nanocrystals in organic solvent or CdX/YZ fluorescent nanocrystals capped with mercapto-based compound). The comparison of fluorescence intensity was made as previously described.

What is claimed:

1. A functionalized fluorescent nanocrystal comprising:
a fluorescent nanocrystal; and
a coating material disposed on the fluorescent nanocrystal, wherein the coating material comprises an imidazole-containing-compound comprising two or more amino acids joined together, and wherein the coating material is uniformly deposited on the nanocrystal surface.

2. The functionalized fluorescent nanocrystal of claim 1, wherein the fluorescent nanocrystal emits light with a quantum yield of greater than about 10%.

3. The functionalized fluorescent nanocrystal of claim 1, wherein the fluorescent nanocrystal emits light with a quantum yield of greater than about 50%.

4. The functionalized fluorescent nanocrystal of claim 1, wherein the fluorescent nanocrystal is soluble in a fluid with a surface energy of greater than 35 dynes/em.

5. The functionalized fluorescent nanocrystal of claim 1, wherein the functionalized fluorescent nanocrystal is soluble in an aqueous solution.

6. A composition, comprising the functionalized fluorescent nanocrystals according to claim 5.

7. The composition according to claim 6, wherein the functionalized fluorescent nanocrystal is dispersed in the aqueous solution and exhibits luminescence when excited by an appropriate energy source.

8. The functionalized fluorescent nanocrystal of claim 1, wherein the coating material is bound to a molecular probe.

9. The functionalized fluorescent nanocrystal of claim 8, wherein the molecular probe is an affinity molecule.

10. The functionalized-fluorescent nanocrystal of claim 8, wherein the molecular probe is selected from the group consisting of avidin, ConA, lectins, monoclonal antibodies, peptides, aptamers, nucleic acid molecules, oligonucleotides, nucleobases, and IgG.

11. The functionalized fluorescent nanocrystal of claim 1, wherein the fluorescent nanocrystal has a characteristic spectral emission intensity which is enhanced by the coating material.

12. The functionalized fluorescent nanocrystal of claim 1, wherein the fluorescent nanocrystal comprises a core material and a capping layer.

13. The functionalized fluorescent nanocrystal of claim 12, wherein the imidazole-containing compound is operably bound to the capping layer.

14. The functionalized fluorescent nanocrystal of claim 1, wherein the coating material further comprises a phosphine cross-linking compound.

15. The functionalized fluorescent nanocrystal of claim 1, wherein at least one or two or more amino acids joined together is histidine.

16. A method for detecting a target species, comprising:
exciting a complex formed by operably bonding a fluorescent nanocrystal according to claim 1 to a target molecule to form a complex; and
detecting the light emitted from the complex.

17. The method of claim 16, wherein the detecting further comprises detecting the intensity of light emitted from the complex in the perpendicular and parallel directions.

18. A process for the preparation of a functionalized fluorescent nanocrystal, comprising contacting a fluorescent nanocrystal comprising a core material and a capping layer with an imidazole-containing compound comprising two or more amino acids joined together to form a coating material on the fluorescent nanocrystal, wherein the imidazole-containing compound is operably bound to the capping layer, and wherein the coating material is uniformly deposited on the nanocrystal surface.

19. The process of claim 18, further comprising contacting the fluorescent nanocrystal with a phosphine cross-linking compound.

* * * * *